United States Patent [19]

Musso et al.

[11] Patent Number: 4,939,224
[45] Date of Patent: Jul. 3, 1990

[54] VASOACTIVE INTESTINAL PEPTIDE ANALOGS

[75] Inventors: Gary F. Musso, Encinitas, Calif.; Emil T. Kaiser, New York, N.Y.; Gönül Velicelebi, San Diego, Calif.

[73] Assignee: The Salk Institute Biotechnology/Industrial Associates, Inc., San Diego, Calif.

[21] Appl. No.: 146,463

[22] Filed: Jan. 21, 1988

Related U.S. Application Data

[63] Continuation-in-part of Ser. No. 19,148, Feb. 26, 1987, Pat. No. 4,835,252.

[51] Int. Cl.$^5$ ................................................ C07K 7/10
[52] U.S. Cl. ...................................................... 530/324
[58] Field of Search .......................................... 530/324

[56] References Cited

U.S. PATENT DOCUMENTS

| 3,880,826 | 4/1975 | Said et al. | 260/112.5 |
| 4,016,258 | 4/1977 | Said et al. | 260/112.5 |
| 4,119,618 | 10/1978 | Said | 530/324 |
| 4,605,641 | 8/1986 | Bolin et al. | 260/112.5 |
| 4,734,400 | 3/1988 | Bolin et al. | 514/112.5 |
| 4,737,487 | 4/1988 | Watts et al. | 514/15 |
| 4,757,133 | 7/1988 | Ito et al. | 530/324 |
| 4,835,252 | 5/1989 | Musso et al. | 530/324 |

FOREIGN PATENT DOCUMENTS 0184309 6/1911 European Pat. Off. .

OTHER PUBLICATIONS

Musso, Ph.D. Dissertation, University of Chicago, Chicago, Ill., U.S.A. (1983).
Robson et al., "Introduction to Proteins and Protein Engineering", Elsevier, Science publishers B. V. Amsterdam, New York, Oxford, pp. 323-325 (1986).
Beyerman et al., "Synthesis, Biological and Immunochemical Properties of Analogs of Secretin and Vasoactive Intestinal Peptide (VIP): The Vasectrins," Life Sciences 29, 895-802 (1981).
Takeyama et al., "Studies on Peptides. XCVII. Synthesis of Porcine Glu$^8$-Vasoactive Intestinal Polypeptide (VIP)," Chem. Pharm. Bull. 28(7), 2265-2269 (1980).
Bodansky and Natarajan, "Synthesis and Some Pharmacological Properties of the 23-Peptide 15-Lysine-Secretin-(5-27), Special Role of the Residue in Position 15 in Biological Activity of the Vasoactive Intestinal Polypeptide," Journal of Medicinal Chemistry 21, No. 11, 1171-1173 (1978).
Kaiser and Kezdy, "Amphiphilic Secondary Structure: Design of Peptide Hormones," Science 223, 249-255 (1984).
Robberecht et al., "Effects of HIS Modifications on the Ability of Vasoactive Intestinal Peptide to Stimulate Adenylate Cyclase from Rat and Human Tissues," Peptides 5, 877-881 (1984).
Turner et al., "A Fragment of Vasoactive Intestinal Peptide, VIP (10-28), is an Antagonist of VIP in the Colon Carcinoma Cell Line, HT29, " Peptides 7, 849-854 (1986).
James B. D. Palmer, et al., "VIP and PHM and their Role in Nonadrenergic Inhibitory Responses in Isolated Airways," Am. Physiol. Soc., pp. 1322-1328, 1986.
Patrick Robberecht et al., "[D-Phe$^4$] Peptide Histidine-Isoleucinamide ([D-Phe$^4$]PHI), a Highly Selective Vasoactive-Intestinal Peptide (VIP) Agonist, Discriminates VIP-Preferring from Secretin-Preferring Receptors in Rat Pancreatic Membranes," Eur. J. Biochem., 165: 243-249 (1987).
D. McMaster et al., "Iodinated Derivatives of Vasoactive Intestinal Peptide (VIP), PHI and PHM: Purification, Chemical Characterization and Biological Activity,"0 Peptides, vol. 8, pp. 663-676, 1987.
Alain Robichon et al., "Chemical Modification of Guanidinium Groups of Vasoactive Intestinal Peptide," Biochimica et. Biophysica Acta, vol. 923, pp. 250-256, 1987.
Dimaline et al., "A Novel Family of VIP-Like Peptides from the Dogfish Scyliorhinus Canicula," Reg. Peptides, 18: 356, 1987.
Dimaline et al., "The Novel Vasoactive Intestinal Peptide (VIP) from Elasmobranch Intestine has Full Affinity for Mammalian Pancreatic VIP Receptors," Biochim. Biophys. Acta 930, 97-100 (1987).

Primary Examiner—Lester L. Lee
Assistant Examiner—Christina Chan
Attorney, Agent, or Firm—Fitch, Even, Tabin & Flannery

[57] ABSTRACT

Novel, biologically active, 28-amino acid analogs of human vasoactive intestinal peptide are provided.

5 Claims, No Drawings

VASOACTIVE INTESTINAL PEPTIDE ANALOGS

This is a continuation-in-part of U.S. patent application Ser. No. 019,148, filed Feb. 26, 1987, now U.S. Pat. No. 4,835,252.

BACKGROUND OF THE INVENTION

Vasoactive intestinal peptide is a known, 28-amino acid, carboxy-terminal-amidated peptide hormone. The sequence of human vasoactive intestinal peptide (hereinafter "VIP"), which is the same as that of bovine, porcine and rat vasoactive intestinal peptide, is as follows:

H-S-D-A-V-F-T-D-N-Y-T-R-L-R-K-Q-M-A-V-K-K-Y-L-N-S-I-L-N-$NH_2$, wherein the "$NH_2$" at the carboxy-terminus indicates carboxy-terminal amidation. (See Table A, below, for definitions of the one-letter abbreviations used herein for amino acids).

The presence of VIP has been documented in the neuronal cell structures of the brain, the genito-urinary tract, the tracheobronchial tract and the nasal mucosa, the exocrine glands, including salivary, sweat, pancreas and lacrymal glands, the nerve fibers of many peripheral endocrine organs, the peripheral nervous system, and cells of the gastrointestinal tract.

The numerous and varied biological activities associated with VIP include: (1) neuroregulation; (2) inducement of vasodilation; (3) smooth muscle relaxation; (4) stimulation of the intestinal secretion of water and electrolytes; (5) regulation of water and electrolyte transport in various tissues; (6) inhibition of gastric acid secretion; (7) promotion of glycogenesis; and (8) stimulation of the production of pancreatic juice. As a result of its many biological activities, VIP has a number of potential therapeutic uses.

In connection with its mediation of smooth muscle relaxation, VIP can be utilized in reversing broncheal obstruction due to asthmatic bronchospasm. In vitro and in vivo testing have shown VIP to relax tracheal smooth muscle and protect against bronchoconstrictor agents such as histamine and prostaglandin. Wasserman et al. in Vasoactive Intestinal Peptide, ed, S. I. Said, 177–184, Raven Press, N.Y. 1982; Said et al. Ann N.Y. Acad. Sci. 221, 103–117 (1974); Morice et al., Lancet 1983, ii: 1225–1227; Barnes and Dixon, Am. Rev. Resp. Dis. 130, 162–166 (1984); Morice and Sever, Thorax 39, 707 (1984); Altiere and Diamond, J. Appl. Physiol.: Resp. Env. Ex. Physiol. 56, 986–992 (1984); Altiere and Diamond, Br. J. Pharm. 82, 321–328 (1984); Hand et al., Eur. J. Pharm. 98, 279–284 (1984).

VIP causes bronchodilation when administered intravenously or by inhalation. Intravenous administration has drawbacks, in that the VIP is not limited to specific tissues and has a number of effects other than bronchodilation which are usually considered to be deleterious (i.e. hypotension, tachycardia, flushing). Administration by inhalation is more tissue specific and has fewer side-effects than intravenous administration but appears to be less effective than intravenous administration. Altiere et al., Pharmacologist 25, 123 (1983); Bundgaard et al., Eur. J. Respir. Dis. 64 (Suppl. 128), 427–429 (1983); Barnes and Dixon (1984), supra; Altiere et a)., Chest 86, 153–154 (1984).

The lower efficacy of VIP in bronchodilation when administered by inhalation, in comparison with administration intravenously, is thought to be caused by either (1) rapid degradation of VIP by compounds, including proteolytic enzymes, present in the respiratory tract both in the bronchial airways and the passageways leading thereto (Barrowcliffe et al., Thorax 41, 88–93 (1986)) or (2) limited absorption of VIP through nasal and pulmonary mucosa, due in part to the size of VIP (about 3300 daltons)(Effros and Mason, Am. Rev. Resp. Dis. 127, S59–S65 (1982); Altiere et al. Chest 86 153–154 (1984)) The net effect of these factors is to prevent VIP from reaching its receptor in lung tissue, as it must in order to have a bronchodilating effect. Hence, there exists a need for biologically active analogs of VIP that, in comparison with native VIP, are more resistant to proteolytic and other forms of degradation and are better able to reach VIP receptors, or capable of binding with greater affinity to VIP receptors.

Reduced susceptibility to proteolysis would be an advantageous property of a VIP analog for another reason as well. Such reduced susceptibility would improve the efficiency of producing the analog by recombinant DNA techniques. Microbial or animal host cells employed in syntheses by recombinant DNA techniques often contain proteases that degrade heterologous proteins sought to be synthesized by such techniques and thereby reduce the yields of the desired heterologous protein products.

It would also be desirable to have biologically active VIP analogs that are not amidated at the carboxy-terminus. Such analogs would be easier to make, by both recombinant DNA and chemical techniques, than native VIP or other carboxy-terminal-amidated analogs.

Finally, the naturally occurring VIP has so many biological activities that its use is limited, because beneficial effects are associated unavoidably with significant, deleterious side-effects, especially when the VIP is administered intravenously. Thus, it would be desirable to have analogs with effective doses for particular, desirable biological activities of naturally occurring VIP that are decreased relative to the effective doses for other, undesirable activities of the naturally occurring peptide Naturally occurring VIP and fowl vasoactive intestinal peptide are disclosed in Said et al., U.S. Pat. Nos. 3,880,826 and 4,016,258 respectively. VIP is a member of the secretin family of peptides, which includes, besides VIP, secretin, glucagon, gastric inhibitory peptide, peptide histidine-isoleucine, peptide histidine-methionine, and the amino-terminal 29 amino acids of growth hormone releasing factor. See e.g., Itoh et al., Nature 304, 547–549 (1983).

A number of VIP analogs are known. See, e.g., Bolin et al., U.S. Pat. No. 4,605,641; Couvineau et al., Biochem. Biophys. Res. Comm. 121, 493–498 (1984); Beyerman et al., Life Sciences 29, 895–902 (1981); Takeyama et al., Chem. Pharm. Bull. 28, 2265–2269 (1980); Gardner et al., Endocrinol. (Japan.) S.R. No. 1, 1–5 (1980); Bodanszky et al., J. Med. Chem. 21, 1171–1173 (1978); and Bodanszky et al., proc. Nat. Acad. Sci. (U.S.A.) 70, 382–384 (1973).

Although some aspects of the interaction of VIP with its receptors have been described (Laburthe et al., Eur. J. Biochem. 139:181 (1984)), virtually no information which describes the relationship between hormone structure and its affinity for binding to receptors exists in the literature.

Analyses of the secondary structures of certain peptide hormones for amphiphilicity have proven useful in the design of analogs of the hormones which bind, with affinities comparable to the natural hormones, to the specific receptors for the hormones. Kaiser et al., Science 223, 249-255 (1984). Such analyses, and design of analogs based on the analyses, have been carried out for growth hormone releasing factor and glucagon. Musso, Ph.D. Dissertation, University of Chicago, Chicago, Ill. U.S.A. (1983); Kaiser et al., supra. It is recognized, however, that analysis of the secondary structure of a peptide hormone for amphiphilicity, while it might suggest design of analogs that bind with high affinity to the hormone's receptors, is not useful in predicting other properties of the hormones, including, most importantly, biological activity and potency, which depend on numerous, ill-understood factors besides receptor affinity.

SUMMARY OF THE INVENTION

Novel, 28-amino acid analogs of human VIP have been discovered which have one or more of the biological activities of the naturally occurring VIP. The analogs of the invention differ from the naturally occurring peptide at one or more of residues 5-28 and are optionally acetylated at the amino-terminal residue and optionally non-amidated at the carboxy-terminus.

By comparing receptor-binding affinities and ED50's in in vitro tests for biological activity of analogs of the invention with those of human and other naturally occurring VIP's, it has been discovered that VIP activities, of the more active analogs and the naturally occurring peptides, can be rationalized by these peptides, having, at least when bound to a VIP receptor, an amphiphilic secondary structure, wherein residues 6-28 are in a pi-helical conformation with one side of the helix (residue nos. 7, 8, 11, 12, 15, 16, 20, 21, 24, 25 and 28) consisting of charged or uncharged polar residues and the other side, (residue nos. 6, 9, 10, 13, 14, 17, 18, 19, 22, 23, 26 and 27) with the exception of residue 9 (uncharged polar) and residue 14 (basic polar), consisting of hydrophobic residues.

DETAILED DESCRIPTION OF THE INVENTION

The present invention entails novel, biologically active analogs of vasoactive intestinal peptide with the formula:

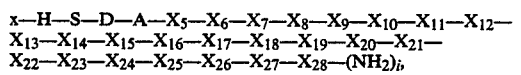

wherein x is selected from the group consisting of $CH_3(CO)-$, $CF_3(CO)-$ and $H-$; wherein $X_5$ is selected from the group consisting of L and V; wherein $X_6$, $X_{10}$, and $X_{22}$ are the same or different and are each selected from the group consisting of F and Y; wherein $X_7$, $X_9$, $X_{11}$, $X_{16}$, and $X_{24}$ are the same or different and are each selected from the group consisting of T, S, L, K, Q, N, R and A; wherein $X_8$ is selected from the group consisting of D, S and A; wherein $X_{12}$ and $X_{20}$ are the same or different and are each selected from the group consisting of K, S, R and O; wherein $X_{13}$, $X_{23}$ and $X_{26}$ are the same or different and are each selected from the group consisting of F, Y, L, I, V, A, and J; wherein $X_{14}$ and $X_{21}$ are the same or different and are each selected from the group consisting of K, R, L, O and J; wherein $X_{15}$ is selected from the group consisting of K, R, S, Q and O; wherein $X_{17}$ and $X_{19}$ are the same or different and are each selected from the group consisting of M, L, V, K, I and J; wherein $X_{18}$ is selected from the group consisting of A and L; wherein $X_{25}$ is selected from the group consisting of S, N, L, A, T and Q; wherein $X_{27}$ is selected from the group consisting of A, L and V; wherein $X_{28}$ is selected from the group consisting of T, N and A; and wherein i is 0 or 1, wherein 0 indicates that the peptide is not carboxy-terminal-amidated and 1 indicates that the peptide is carboxy-terminal-amidated. See Table A below, for the amino acids represented by the one-letter abbreviations.

Preferred among these analogs are those wherein x is selected from the group consisting of H— and $CH_3(CO)-$; wherein $X_5$, $X_{26}$ and $X_{27}$ are the same or different and are each selected from the group consisting of L and V; wherein $X_6$ is F; wherein $X_7$, $X_{24}$ and $X_{25}$ are the same or different and are each selected from the group consisting of S, N and T; wherein $X_8$ is selected from the group consisting of D, S and A; wherein $X_9$ is selected from the group consisting of S, N, and A; wherein $X_{10}$ and $X_{22}$ are Y; wherein $X_{11}$ is selected from the group consisting of S and T; wherein $X_{12}$ is selected from the group consisting of R and K; wherein $X_{13}$ is selected from the group consisting of L, F, V and I; wherein $X_{14}$ is selected from the group consisting of K, R, O and J; wherein $X_{15}$, $X_{20}$ and $X_{21}$ are the same or different and are each selected from the group consisting of R, K, and O; wherein $X_{16}$ is selected from the group consisting of S, N, Q and T; wherein $X_{17}$ is selected from the group consisting of M, V, L, I and J; wherein $X_{18}$ is A; wherein $X_{19}$ is selected from the group consisting of V and I; wherein $X_{23}$ is selected from the group consisting of L, V, I and J; wherein $X_{28}$ is selected from the group consisting of T, N and A; and wherein i is 1.

Exemplary of the analogs of the invention are the following:

Analog 1:
H-S-D-A-V-Y-S-D-S-F-S-R-Y-R-R-S-V-A-L-R-R-F-V-S-N-V-V-T-(NH$_2$);

Analog 2:
H-S-D-A-V-Y-S D-S-F-S-R-Y-R-S-R-V-A-L-S-R-F-V-R-N-V-V-T-(NH$_2$);

Analog 3:
H-S-D-A-V-Y-S-D-S-F-R-S-Y-R-S-R-V-A-L-S-R-F-V-R-N-V-V-T-(NH$_2$);

Analog 4:
H-S-D-A-V-Y-T-D-N-F-S-R-Y-R-K-Q-V-A-L-K-K-F-V-N-S-V-V-T-(NH$_2$);

Analog 5:
H-S-D-A-V-F-S-D-S-Y-S-T-F-R-R-S-M-A-V-R-R-Y-L-S-N-V-L-T-(NH$_2$);

Analog 6:
H-S-D-A-V-Y-S-D-S-F-S-R-F-R-K-Q-M-A-V-K-K-Y-L-N-S-V-L-T-(NH$_2$);

Analog 7:
H-S-D-A-V-F-T-D-N-Y-S-R-Y-R-R-Q-M-A-V-K-K-Y-L-N-S-V-L-T-(NH$_2$);

Analog 8:
H-S-D-A-V-F-T-D-H-Y-S-R-F-R-K-S-V-A-V-K-K-Y-L-N-S-V-L-T-(NH2);

Analog 9:
H-S-D-A-V-F-T-D-N-Y-S-R-F-R-K-Q-M-A-V-R-R-F-V-N-S-V-L-T-(NH2);

Analog 10:
H-S-D-A-V-F-T-D-N--Y-S-R-F-R-I-Q-M-A-V-K-K-Y-L-S-N-V-V-T-(NH2);

Analog 20:
H-S-D-A-L-F-S-D-A-Y-S-K-L-K-K-S-L-A-L-K-K-Y-L-S-S-L-L-A-(NH2);

Analog 20-X:
CH3(CO)-H-S-D-A-L-F-S-D-A-Y-S-K-L-K-K-S-L-A-L-K-K-Y-L-S-S-L-L-A-(NH2);

Analog 28:
H-S-D-A-V-F-T-D-S-Y-S-R-F-L-K-S-L-A-V-K-K-Y-L-S-S-L-L-T-(NH2);

Analog 33
H-S-D-A-V-F-S-D-S-Y-S-K-F-R-K-S-J-A-V-K-K-Y-L-S-S-V-L-T-(NH2);

Analog 34
H-S-D-A-V-F-T-D-N-Y-S-R-L-K-R-S-J-A-V-R-R-Y-L-S-S-V-L-T-(NH2);

Analog 35
H-S-D-A-V-F-T-D-A-Y-S-R-L-J-R-S-J-A-V-R-R-Y-L-S-S-V-L-T-(NH2); and

Analog 36
H-S-D-A-V-F-T-S-T-Y-S-R-L-J-R-S-J-A-V-R-R-Y-L-S-S-V-L-T-(NH2).

Also exemplary of the analogs of the invention are the analogs, of the above-illustrated exemplary analogs, which are not amidated at the carboxy-terminus.

More preferred among the preferred analogs of the present invention are carboxy-terminal amidated analogs 5, 20, 20-X, 28, 33, 34, 35 and 36. Most preferred is carboxy-terminal amidated analog 5.

It is intended that an analog is also within the scope of the present invention if it is essentially equivalent to an analog of the invention, as specified above. An analog is essentially equivalent to one specified above if it has one or more of the biological activities characteristic of human VIP, has the same number of amino acids as the specified analog and, in comparison with the sequence of the specified analog, has at most five amino acid substitutions, all of which would be considered neutral in the art (i.e., acidic for acidic, basic for basic, uncharged polar for uncharged polar, hydrophobic for hydrophobic, and the like).

The acidic amino acids are Asp, Glu and gammacarboxyglutamic acid. The basic amino acids are Arg, Lys, His and Orn. The hydrophobic amino acids are Ala, Ile, Leu, Met, Nor, Phe, Trp, Tyr, Val, t-butylglycine, norvaline, cyclohexylalanine, t-butylalanine, amino-4phenylbutyric acid, beta-2-thienylalanine, p-bromophenylalanine, p-chlorophenylalanine, p-iodophenylalanine, p-nitrophenylalanine, 3,5-diiodotyrosine, phenylglycine, and napthylalanine. Uncharged polar amino acids are Asn, Gln, Ser, and Thr. Gly can be substituted for an uncharged polar or a hydrophobic amino acid, but substitutions with Gly are avoided because helical structures may be destabilized by such a substitution. Substitutions with Pro are generally avoided because of a significant effect on secondary structure of inserting a Pro in place of another amino acid. Substitutions with Cys are generally avoided because of the reactivity of the sulfhydryl group.

The chiral amino acids of the VIP analogs of the invention have the L configuration. The amino acids are identified in the present application according to the three-letter or one-letter abbreviations in the following Table A:

TABLE A

| Amino Acid | Three-Letter Abbreviation | One-Letter Abbreviation |
| --- | --- | --- |
| L-Alanine | Ala | A |
| L-Arginine | Arg | R |
| L-Asparagine | Asn | N |
| L-Aspartic Acid | Asp | D |
| L-Cysteine | Cys | C |
| L-Glutamine | Gln | Q |
| L-Glutamic Acid | Glu | E |
| Glycine | Gly | G |
| L-Histidine | His | H |
| L-Isoleucine | Ile | I |
| L-Leucine | Leu | L |
| L-Lysine | Lys | K |
| L-Methionine | Met | M |
| L-Norleucine | NorLeu | J |
| L-Ornithine | Orn | O |
| L-Phenylalanine | Phe | F |
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |

"Asx" means Asp or Asn.
"Glx" means Glu or Gln.

Analog 1 was designed as a pi-helical secondary structural mimic of VIP from amino acid residues 6 to 28. Analog 1 contains only 28% overall homology with the amino acid sequence of human VIP.

It has been suggested that the degradation of VIP occurs predominantly between the pairs of basic amino acid residues at positions 14–15 and 20–21 (Bodanzsky et al., Bioorg. Chem. 8:399 (1979)). Thus, in VIP analogs 2 and 3, the pairs of basic amino acid residues, residues 14–15 and 20–21, were separated in order to reduce the susceptibility of the peptide analogs to proteolysis by serine proteases. However, proteolytic stability assays, which were performed on such analogs, and which are described in the Examples below, indicated that all of the analogs tested were comparable to VIP in terms of half-life in the presence of proteases. This result suggests that removal of pairs of basic amino acid residues does not decrease susceptibility of the analogs to proteolysis by proteases, as analogs 2 and 3, which do not have pairs of basic amino acids, did not have increased proteolytic stability. Stability results for analogs 2 and 3 indicated that other factors contribute to the proteolytic degradation of VIP and the analogs. Separation of the above-described pairs of basic amino acid residues may have resulted in greater conformational freedom in these analogs and, thus, greater exposure of the peptide backbone to proteolytic enzymes.

Analogs 4 and 5 were designed as hybrids between VIP and analog 1 in order to investigate the functional role of each face of the pi-helical cylindrical segment, residues 6–28. While analog 4 employed amino acids present in VIP on the hydrophilic surface (i.e., residues 7, 8, 11, 12, 15, 16, 20, 21, 24, 25, and 28), and those present in analog 1 on the hydrophobic surface (i.e., residues 6, 9, 10, 13, 14, 17, 18, 19, 22, 23, 26 and 27), analog 5 was designed in the opposite manner (i.e., follow VIP on hydrophobic surface and analog 1 on hydrophilic).

Analog 5, which contains an idealized hydrophobic surface, was found to be an effective VIP agonist. The affinity and potency of this analog is comparable to that of VIP in the assay systems described in the Examples. The high biological activity which has been displayed by analog 5, and which is described in the Examples below, provides support for the validity of the working hypothesis of the existence of an amphiphilic pi-helix in the secondary structure of residues 6–28 of VIP when bound to VIP receptors. Comparison of the potencies of analogs 4 and 5, which is also set forth in the Examples below, indicates that the biological activities of analogs of VIP are more sensitive to changes in the hydrophobic surface of this amphiphilic pi-helix than to changes in the hydrophilic surface. Consequently, it appears that amino acid residues which are essential for binding to VIP receptors are present on the hydrophobic surface of the pi-helical cylinder. More specifically, amino acid residues which have been found to be important for recognition of high affinity VIP receptors which are described further in the Examples, are contained on the hydrophobic surface of the helical segment.

In contrast, activity data obtained from several of the other analogs suggests that the amino acid residues which are present on the hydrophilic surface of the helical segment, with the exception of Arg-12, neither participate strongly in a receptor binding process nor affect cellular responses significantly. It appears that preserving Arg at position-12 is important for activity.

In each of analogs 1–10 described above, amino acid 9 was preserved as an uncharged polar amino acid and amino acid 14 was preserved as an hydrophilic amino acid in an otherwise hydrophobic environment.

Amidation of the carboxyl-terminus of the various VIP analogs was found to enable optimal binding of the analogs to the VIP receptors. The amidated forms of the VIP analogs displayed a 10-fold higher receptor binding affinity than those forms which were non-amidated.

The following conclusions regarding the relationship between the structure and function of amino acids within the sequence of VIP, which were drawn from biochemical studies of VIP and analogs 1–10, provide critical information about the essential requirements of the VIP sequence for proper receptor interaction: (1) The pi-helical conformational model of residues 6–28 is valid as a structural basis for VIP analog design; (2) The hydrophobic surface residues appear to be essential for effective interaction with functional receptors; (3) Specific hydrophilic or uncharged polar amino acids are not required on the hydrophilic surface; (4) A blocked carboxyl-terminal is necessary for maximum binding affinity; and (5) Results of the proteolytic stability study indicate that arginine may be a poor choice for a basic residue, since the analogs containing arginine in place of lysine appear to be more susceptible to degradation.

The results obtained with analogs 1–10 showed that the hydrophobic surface of the pi-helical domain contains amino acids important for interaction with membrane VIP receptors, whereas amino acid residues on the hydrophilic surface do not appear to participate strongly in receptor binding or in signal transduction. Furthermore, the effects of VIP and the novel analogs of the present invention appeared to be coupled to the higher affinity membrane VIP receptors described in Example II.

The results obtained with analogs 1–10, as well as those reported in the literature, also suggested that the functionally important amino acid residues may be present in a linear array, which twists slightly with the hydrophobic surface of the pi-helix. Six amino acids are in this linear array that are thought to be functionally important, as follows: Phe-6, Tyr-10, Arg-12, Ala-18, Tyr-22 and Leu-27. (Comparison of sequences of vasoactive intestinal peptides of several species, peptides related thereto, and active as well as inactive analogs thereof, indicated that the following amino acid residues are invariant and, perhaps, critically important to VIP function: His-1, Ser-2, Asp-3, Ala-4, Phe-6, Asp-8, Tyr-10, Arg-12, Ala-18, Tyr-22, Leu-27.)

Leucine and lysine had been avoided in analogs 1–10 due to their potential for promoting an alpha-helical, as opposed to a pi-helical, conformation. However, the significantly higher occurrence of leucine and lysine in the VIP-secretin-glucagon superfamily than in proteins generally indicated that these two amino acid residues may be preferred in the folding of the pi-helix. Consequently, in analog 20, leucine and lysine were used as the hydrophobic and basic residues, respectively, while serine and aspartate, which had been found to promote activity among analogs 1–10, were maintained as uncharged polar and acidic residues, respectively. Further, lysine was chosen because use of arginine was found not to provide any enhancement of stability against proteolysis. In addition, residues 1 through 4, 6, 10, 18, 22, and 27 were chosen to be those which occur, at the respective positions, in chicken vasoactive intestinal peptide, the most potent of naturally occurring vasoactive intestinal peptides in various in vitro tests for bioactivity on mammalian tissue. Further, residue 8 was maintained as Asp.

In analog 20, the asparagine at position 9 on the "hydrophobic face" was replaced with alanine, to reduce deviation of the hydrophobic face from hydrophobicity.

Analog 20 was synthesized in two forms. In one form, the analog was acetylated at the amino-terminus whereas in the other form it was non-acetylated at the amino-terminus. It was thought that acetylation could slow the proteolytic degradation of the peptide and, thus, enhance its apparent bioactivity.

Analogs 28 and 33 were designed as hybrids between analog 5 and analog 20 in an attempt to combine the higher biological potency of analog 5 with the apparent tissue selectivity of analog 20. Thus, most of the hydrophobic surface from analog 5 was combined with most of the hydrophilic surface from analog 20. Additionally, analog 28 addresses the role of the hydrophilic violations, Arg-14 and Asn-9, in the functional coupling of VIP with its receptors. Thus, Arg-14 has been replaced by Leu in this analog. Also, in analog 33, norleucine has been substituted for methionine in position 17 in an attempt to increase the affinity for binding to VIP receptors.

Analogs 34–36, which were designed with the use of data obtained from the analysis of analogs 1 through 10, 20, 28 and 33 in various assays, were based on the amino acid sequence of analog 5. However, those residues of analog 5 which were thought to weaken the affinity of the analog for VIP receptors were substituted with amino acid residues which appeared to increase the potency of the peptide in receptor-binding. Thus, in analog 34, Thr was used in position-7, Asn was used in position 9, Leu was used in position-13, Lys was used in position-14, NorLeu was used in position-17, and Ser was used in position-25.

Additional modifications, which seem to increase biological potency in the various assays described herein, may be made at positions 9 and 14. Amino acids more hydrophobic than arginine, such as Lys and NorLeu at position-14 have a positive effect on the binding of the peptide to lung VIP receptors. The employment of Val at position-26 and Thr at position-28 has a similar effect Thus, in analog 35, Ala was employed at position-9 and NorLeu was used at position-14. Analog 36 employs Thr at position-9 and NorLeu at position-14.

An analog of the present invention can be made by exclusively solid phase techniques, by partial solid-phase techniques, by fragment condensation, by classical solution coupling, or, as long as the analog consists of only amino acids among the twenty naturally occurring amino acids corresponding to codons of the genetic code, by employing recombinant DNA techniques with bacteria, such as *E. coli* or *B. subtilis;* yeast, such as *S. cerevisiae* or *P. pastoris;* or mammalian cells.

Methods of making a polypeptide of known sequence by recombinant DNA techniques are well-known in the art. See, e.g., U.S. Pat. No. 4,689,318, which is incorporated herein by reference. Methods for amidating at the carboxy-terminus peptides that have been made by recombinant DNA techniques are also known. See, e.g., U.S. Pat. No. 4,708,934, also incorporated herein by reference.

Methods for chemical synthesis of polypeptides are also well-known in the art and, in this regard, reference is made, by way of illustration, to the following literature: Yamashino and Li, J. Am. Chem. Soc. 100, 5174–5178 (1978); Stewart and Young, Solid Phase Peptide Synthesis (W.H. Freeman and Co. 1969); Brown, et al., J. C. S. Perkin I, 1983, 1161–1167; M. Bodanszky, et al., Bioorg. Chem. 3, 320–323 (1974); E. Atherton, et al., J. C. S. Perkin I, 1981, 538–546; S. R. Pettitt, Synthetic Peptides, (Elsevier Scientific Publishing Co. 1976); Y. S. Klausner and Bodanszky, Bioorg Chem. 2, 354–362 (1973); U.S. Pat. Nos. 4,689,318; 4,632,211; 4,237,046; 4,105,603; 3,842,067; and 3,862,925, all or which are incorporated herein by reference.

Preferred, automated, step-wise solid-phase methods for synthesis of peptides of the invention are provided in the examples below.

The VIP analogs encompassed by the present invention have one or more of the biological activities of naturally occurring VIP, as described above, and, as such, are useful therapeutically in one or more of the ways in which VIP is known to be useful, e.g., to relieve bronchoconstriction in a mammal suffering from asthma or exposed to an untoward amount of a bronchoconstrictor such as histamine or a prostaglandin; to reduce blood pressure in a mammal suffering from hypertension; or to inhibit gastric acid secretion in a mammal suffering from a disease, such as ulcers, due to or exacerbated by excessive gastric acid secretion.

The biological activity of an analog of the invention is determined by comparing the analog with naturally occurring VIP in a lung-strip assay for VIP-induced muscle relaxation (Saga and Said, Trans. Assoc. Am. Physicians 7, 304–310 (1984)), a mammalian trachea or stomach fundus strip relaxation assay, or an assay for stimulation of amylase secretion from mammalian pancreatic acinar cells. Other important properties of analogs of the invention are determined by a radio-receptor assay for binding of the analog to vasoactive intestinal peptide-receptor in mammalian lung membrane, and an homogenized mammalian lung assay for evaluating the resistance of an analog to proteolytic degradation. Rat or guinea pig tissues are commonly employed in such assays.

Data for analogs of the invention from various assays are presented in the examples below.

The analogs of the invention are employed therapeutically, under the guidance of a physician, to reduce hypertension in a person suffering therefrom or to reduce bronchoconstriction in a person suffering from asthma or exposed to an untoward, bronchoconstricting concentration of a bronchoconstrictor such as histamine or a prostaglandin The preferred use of the analogs of the invention is in relieving bronchoconstriction due to asthma in persons suffering therefrom.

The dose and dosage regimen of an analog according to the invention that is suitable for administration to a particular patient can be determined by a physician considering the patient's age, sex, weight, general medical condition, and the specific condition and severity thereof for which the analog is being administered; the route of administration of the analog; the pharmaceutical carrier with which the analog may be combined; and the analog's biological activity, relative to that of naturally occurring human VIP, in the above-described assays.

Generally, intravenous injection of 1–50 pmol of analog/kg body weight/minute, by bolus injection or by infusion over a period of about 5 minutes to about 60 minutes, is sufficient to reduce hypertension or relieve bronchoconstriction. Aerosol inhalation of 0.1 to 2 mg of analog/kg body weight is also sufficient for relief of bronchoconstriction.

Intravenous administration, by bolus injection or continuous infusion, is preferred for use of the analogs of the invention in treatment of hypertension.

For use of the analogs in relieving broncho-constriction, administration by inhalation of an aerosol containing an analog of the invention is preferred.

The analogs of the invention, or a pharmaceutically acceptable salt thereof, can be combined, over a wide concentration range (e.g., 0.001 to 1.0 wt %) with any standard pharmaceutical carrier (e.g., physiological saline, THAM solution, or the like) to facilitate administration by any of various routes including intravenous, subcutaneous, intramuscular, oral, or intranasal, including by inhalation.

Pharmaceutically acceptable acid addition salts of the analogs of the invention can be prepared with any of a variety of inorganic or organic acids, such as, for example, sulfuric, phosphoric, hydrochloric, hydrobromic, nitric, citric, succinic, acetic, benzoic and ascorbic. The analogs can, for example, be advantagously converted to the acetate salt by dissolution in an aqueous acetic acid solution (e.g., 10% solution) followed by lyophilization.

The invention will now be illustrated in greater detail in the following examples

EXAMPLE I

Preparation of VIP Analogs

Peptides were synthesized using solid-phase methodology, generally described by Merrifield (J. Amer. Chem. Soc., 85, 2149 (1963)) (see also Stewart and Young, supra.) with various modifications described herein, carried out on a Beckman 990B automated peptide synthesizer (Beckman Instruments, Inc., Fullerton, Calif., U.S.A.).

Sequential assembly of a peptide analog is conducted from the carboxy-terminus, bonded to a solid-phase resin, to the amino terminus; the addition of amino acids to a peptide chain is automated after the attachment of the carboxy-terminal amino acid to the resin.

For peptides that will have a carboxyl group at the carboxy-terminus, p-chloromethyl-derivatized polystyrene supports are employed, and the carboxy-terminal amino acid is esterified to the support via reaction with KF as described by Horiki, et al., Chem Lett. 1978, 165–168. For peptides which are amidated at the carboxy-terminus, p-methylbenzhydrylamine-derivatized (i.e., "MBHA"-derivatized) polystyrene supports or p-benzhydryl-amine-derivatized (i.e., "BHA"-derivatized) polystyrene supports are employed, and the carboxy-terminal amino acid is attached to the support via dicyclohexylcarbodiimide-mediated coupling followed by acetylation of the unreacted amine sites on the support with acetyl imidazole. Following attachment of the carboxy-terminal amino acid to the support, the level of substitution of the amino acid on the support is determined by the picric acid titration method described by Gisin, Anal. Chim. Acta, 58, 248–249 (1972). Substitution levels for automated syntheses are preferably between 0.2 and 0.6 mmol amino acid per g resin. A typical synthesis is performed on a scale of 0.25–1.0 mmol and thus is initiated with 0.4–2.5 g amino acid-derivatized resin. Steps in the syntheses of the VIP analogs employed the following Protocol I(a):

| PROTOCOL I(a) | | | |
|---|---|---|---|
| STEP | REAGENT | MIX TIME (MIN.) | # OF TIMES |
| 1 | Methylene Chloride | 0.5 | 4 |
| 2 | 50% TFA/Methylene Chloride/ 1% Ethanedithiol | 1 | 1 |
| 3 | 50% TFA/Methylene Chloride/ 1% Ethanedithiol | 20 | 1 |
| 4 | Methylene Chloride | 1 | 3 |
| 5 | Isopropanol | 1 | 2 |
| 6 | Methylene Chloride | 1 | 2 |
| 7 | 5% DIEA/Methylene Chloride | 2 | 2 |
| 8 | Methylene Chloride | 1 | 1 |
| 9 | 5% DIEA/Methylene Chloride | 2 | 2 |
| 10 | Methylene Chloride | 1 | 3 |
| 11 | Amino Acid | Variable | 1 |
| 12 | Methylene Chloride | 1 | 2 |
| 13 | Dimethylformamide | 1 | 2 |
| 14 | 33% Methanol/Methylene Chloride | 1 | 2 |
| 15 | Stop or Return for Next Coupling | | |

Methylene chloride, dimethylformamide (DMF), and isopropanol were reagent grade and stored over 4 A molecular sieves. Ethanedithiol, 1-hydroxybenzotriazole (HOBT), and diisopropylethylamine (DIEA) were used as purchased from Aldrich Chemical Company (Milwaukee, Wis., U.S.A.). Trifluoroacetic acid (TFA) was freshly distilled prior to use. Dicyclohexylcarbodiimide (DCC) was distilled in vacuo. The coupling of amino acids was usually carried out for 30 minutes with the preformed symmetric anhydride of the amino acid involved (see Yamashino and Li, supra.) with at least a 3-fold excess of symmetric anhydride with respect to the available amine sites on the resin. Arginine was coupled with DCC using 3.5-fold excess arginine and 3-fold excess DCC in 25% DMF/methylene chloride for 2 hours. Asparagine and glutamine were also dissolved in 25% DMF/methylene chloride and coupled as HOBT-active esters for 2 hours.

The tert-butyloxycarbonyl (BOC) group was used for protection of the alpha amine group of all amino acids employed in the syntheses; however, other protecting groups known in the art for alpha amines can be employed successfully. Side-chain functionalities were protected as follows: Arg and His with p-toluene-sulfonyl; Asp, Glu, Ser, and Thr with benzyl; Lys and Orn with 2-chlorobenzyl-oxycarbonyl; and Tyr with 2,6-dichlorobenzyl.

The resins employed in the syntheses were, for the carboxy-terminated analogs, chloromethyl-derivatized polystyrene-1% divinyl-benzene (200–400 mesh) from U.S. Biochemicals Corp., Cleveland, Ohio, U.S.A.(1.1 milliequivalent Cl/g resin) or, for carboxy-terminal-amidated analogs, MBHA-derivatized or BHA-derivatized polystyrene-1% divinylbenzene (150–200 mesh) from Colorado Biotechnology Associates (Boulder, Colo., U.S.A.) (0.45 milliequivalent NH$_2$/g resin).

After assembly of the completed analog, the amino-terminal BOC group is removed using steps 1–9 of the above protocol and then the resin is washed with methanol and dried. The analogs are then deprotected and removed from the resin support by treatment with HF/anisole for 1 hour at 0° C. Following removal of the HF, the crude analog preparation was washed with 3 portions of ethyl acetate, extracted with 3 portions of 10% acetic acid in water, and then lyophilized.

Either a one-step or a two-step HF cleavage protocol can be employed to remove the analogs from the resin support. The one-step cleavage protocol, which is the simpler of the two protocols, involves cleaving the fully protected peptide off of the resin with 90% HF, 10% anisole for 1 hour at 0° C., followed by ether extraction in 10% HOAc. This process works well for all peptides except those which are susceptible to cation attack, e.g., involving methionine residues. The two-step process employs a 35% HF, 65% DMS, and 10% p-cresol cleavage step at 0° C. for 1 hour, followed by 90% HF, 10% p-cresol for another hour, and then ether extraction as before.

The resulting crude preparations were purified by preparative high performance liquid chromatography (HPLC) on a Zorbax C-8 column (21×250 mm) (DuPont Co., Wilmington, Del. U.S.A.) and analyzed by analytical HPLC with one of four buffers. Preparative HPLC separations were performed with the Zorbax column on a Waters Prep 3000 System (Millipor Corp., Milford, Mass., U.S.A.) at a flow rate of 15 ml/min. Samples were introduced in 50–250 mg portions in 0.1% TFA (running buffer) and eluted from the column with an acetonitrile gradient (20–40%/40–60 minutes). Peptide fractions were monitored by UV absorbance at 230 or 278 nm. In all cases, fractions were manually collected at peak detection. The purified fractions were analyzed on an analytical HPLC (Beckman System 345, Beckman Instruments, Inc.) using an Altex C-18 column (4.6×250 mm) (Beckman Instruments, Inc.) using a buffer system of 0.1% phosphoric acid, 0.1M sodium perchlorate, pH 2.5 and an acetonitrile gradient. Other HPLC buffer systems which may be employed in the analytical HPLC include triethylamine phosphate (TEAP), pH 2.5-3.0, TEAP, pH 6.5, and 0.1% trifluoracetic acid (TFA). The resolving power of the buffer system for these analogs follows the order of $NaClO_4$, $H_3PO_4$>TEAP (pH 2.5) >TFA>TEAP (pH 6.5). Although the TFA buffer system does not resolve microheterogeneous contaminants as well as other systems, recovery is generally 50-90% higher and no further desalting steps are required. A portion of a fraction from the preparative HPLC which appeared homogenous by analytical HPLC was removed, lyophilized and hydrolyzed for amino acid analysis. These portions with the proper amino acid compositions, from the purifications of the various analogs, were then subjected to bioassay.

It should be noted that partition chromatography may be employed to remove several impurities from the crude peptide isolated from HF cleavage prior to the preparative HPLC step. For this step, a two-phase solvent system from the mixing of n-butanol/acetic acid/water (4:1:4) on a support of Sephadex G-25 may be used.

For amino acid analysis, a sample of analog was hydrolyzed in 6N HCl containing 1% phenol for 24 hours at 110° C. Analyses were performed on a Beckman 6300 Amino Acid Analyzer (Beckman Instruments, Inc.) interfaced with a Nelson 3000 Data System (Nelson Analytical, Inc., Cupertino, Calif., U.S.A.).

(a) PREPARATION OF BOC-Thr(OBz)-RESIN

A typical preparation of peptide resin containing threonine, protected with benzyl at the hydroxyl oxygen, as the C-terminal amino acid, is illustrated in the following example: A 10 g portion of p-methylbenzhydrylamine resin (150-200 mesh, 1% crosslinked, 0.45 meq/g (Colorado Biotechnology Associates, Inc.)) was first swelled in 100 ml of methylene chloride. The support, received as the hydrochloride salt, was then neutralized by treatment with 5% DIEA in methylene chloride (2×100 ml for 2 min.). It was washed two more times in methylene chloride. A solution of 1.55 g BOC-Thr(OBz) and 1.03 g DCC in 75 ml of methylene chloride was added to the resin and the mixture was stirred for 2 hours, filtered and washed with methanol (3×75 ml). The resin was then dried overnight in vacuo. The loading of BOC-Thr(OBz) on the resin support was determined by the picric acid titration method described by Gisin, supra. Substitution was determined to be 0.475 mmol/g. The resin was then treated with 550 mg of acetylimidazole in 50 ml of methylene chloride containing 50 μl of triethylamine in order to cap any unreacted amine site on the support.

(b) SYNTHESIS OF THE CARBOXY-TERMINAL-AMIDATED VIP ANALOG 1

The synthesis of Analog 1 H-S-D-A-V-Y-S-D-S-F-S-R-Y-R-R-S-V-A-L-R-R-F-V-S-N-V-V-T-(NH$_2$), amidated at the carboxy-terminus, was initiated by using 475 mg of a BOC-Thr(OBz) resin (substitution level=0.527 mmol/g), prepared following the procedure of Example I(a). All solvents in the automated protocol were metered in 20 ml portions per addition. For couplings requiring symmetric anhydrides, the acylating component was preformed 10 minutes prior to addition by dissolving 6.5-fold excess amino acid with 3-fold excess DCC in 20 ml methylene chloride at 0° C. The resulting dicyclohexylurea was filtered off and the activated component was added to the reaction vessel of the synthesizer. Couplings of Arg, Asn and Gln were done without preactivation and used 15 ml of methylene chloride and 5 ml of DMF. The amount of components is summarized on the following Table I(b):

TABLE I(b)

| CYCLE # | GRAMS OF PROTECTED AMINO ACID | CYCLE # | GRAMS OF PROTECTED AMINO ACID |
|---|---|---|---|
| 1 | 0.353 V | 2 | 0.353 V |
| 3 | 0.261 N, 0.135 HOBT | 4 | 0.479 S |
| 5 | 0.353 V | 6 | 0.430 F |
| 7 | 0.375 R | 8 | 0.374 R |
| 9 | 0.404 L | 10 | 0.307 A |
| 11 | 0.353 V | 12 | 0.479 S |
| 13 | 0.374 R | 14 | 0.374 R |
| 15 | 0.715 Y | 16 | 0.374 R |
| 17 | 0.479 S | 18 | 0.430 F |
| 19 | 0.479 S | 20 | 0.546 D |
| 21 | 0.479 S | 22 | 0.715 Y |
| 23 | 0.353 V | 24 | 0.307 A |
| 25 | 0.546 D | 26 | 0.479 S |
| 27 | 0.796 H | | |

Upon completion of the synthesis, 1 61 g of peptide-resin was obtained. To this was added 2 ml of anisole in an HF reaction vessel and 15 ml of HF was distilled in at −78° C. After 1 hour at 0° C., the HF was removed under vacuum, and the peptide was washed and extracted to yield 725 mg of crude peptide. A 250 mg portion was dissolved in 5 ml of 0.1% TFA containing 20% acetonitrile and injected on the preparative HPLC using the previously described conditions. The purified fractions were analyzed on an analytical HPLC (Beckman System 345, Beckman Instruments, Inc.) using an Altex C-18 column (4.6×250 mm) (Beckman Instruments, Inc.) using a buffer system of 0.1% phosphoric acid, 0.1M sodium perchlorate, pH 2.5, and an acetonitrile gradient. A 10%-60% acetonitrile gradient over minutes was used to elute the peptide components. An aliquot of homogeneous fractions from preparative HPLC was removed, and then hydrolyzed for amino acid analysis. One fraction was homogeneous and gave proper amino acid analysis yielding 6.5 mg of peptide. Amino acid analysis results: Asx (3)3.6, Thr (1)0.7, Ser (6)5.4, Ala (2)2.0, Val (5)5.1, Leu (1)1.0, Tyr (2)2.0, Phe (2)2.2, His (1)0.8, Arg (5)4.9.

(c) SYNTHESIS OF THE CARBOXY-TERMINAL-AMIDATED VIP ANALOG 5

The synthesis of Analog 5: H-S-D-A-V-F-S-D-S-Y-S-R-F-R-R-S-M-A-V-R-R-Y-L-S-N-V-L-T-(NH$_2$), amidated at the carboxy-terminus, was initiated with 1 31 g of a BOC-Thr(OBz) resin (sub. level 0.38 mmol/g; 0.5 mmol scale) prepared following the procedure described in Example I(a). Coupling of sequential amino acids is detailed in the following Table I(c):

TABLE I(c)

| CYCLE # | GRAMS OF PROTECTED AMINO ACID | CYCLE # | GRAMS OF PROTECTED AMINO ACID |
|---|---|---|---|
| 1 | 0.695 L | 2 | 0.625 V |
| 3 | 0.697 N, 0.338 HOBT | 4 | 0.883 S |
| 5 | 0.694 L | 6 | 1.43 Y |
| 7 | 1.285 R | 8 | 1.285 R |
| 9 | 0.652 V | 10 | 0.568 A |
| 11 | 0.748 M | 12 | 0.883 S |

TABLE I(c)-continued

| CYCLE # | GRAMS OF PROTECTED AMINO ACID | CYCLE # | GRAMS OF PROTECTED AMINO ACID |
|---|---|---|---|
| 13 | 1.285 R | 14 | 1.285 R |
| 15 | 0.796 F | 16 | 1.285 R |
| 17 | 0.883 S | 18 | 1.43 Y |
| 19 | 0.883 S | 20 | 0.970 D |
| 21 | 0.883 S | 22 | 0.796 F |
| 23 | 0.652 V | 24 | 0.568 A |
| 25 | 0.970 D | 26 | 0.883 S |
| 27 | 1.471 H | | |

Yield of the dried peptide resin mixture was 3.39 g. A 1.7 g portion of this was cleaved by the two-step HF procedure described by Tam et al., J. Amer. Chem. Soc., 105, 6442–6455 (1983). To the resin was added 3 ml of p-cresol and 19.5 ml dimethylsulfide (DMS) The deprotection was initiated by the addition of 7.5 ml of HF and the reaction mixture was stirred at 0° C. for 2 hours. Following removal of HF and DMS, the resin was washed with ethylacetate and dried. To the crude resin-peptide mix was added 2 ml p-cresol and 18 ml of HF. After stirring for 1 hour at 0° C., the reaction was worked up as in Example I(b). The crude extracted peptide was immediately applied to a Sephadex G-15 column and eluted with 10% acetic acid. The initial major peak was pooled and lyophilized to yield 695 mg of crude peptide. 150 mg of this was purified by preparative HPLC, and analyzed by analytical HPLC as described for Analog 1, yielding 4.2 mg of purified Analog 5 with its proper amino acid composition. Amino acid analysis results were as follows: Asx (3)2.8, Thr (1)1.3, Ser (6)4.4, Ala (2)1.9, Val (3)3.0, Met (1)1.1, Leu (2)2.4, Tyr (2)2.3, Phe (2)1.8, His (1)0.6, Arg (5)5.8.

(d) SYNTHESES OF THE CARBOXY-TERMINAL-AMIDATED VIP ANALOGS 2–4 and 6–10

Carboxy-terminal-amidated analogs 2–4 and 6–10 were synthesized and purified in substantially the same manner as described above for Analogs 1 and 5, beginning with BOC-Thr(OBz)-derivatized p-methylbenzhydrylamine resin, described above in Example I(a), and employing the appropriate protected amino acid in each cycle of the automated synthesis.

Amino acid analysis of analog 2, which was synthesized on a 0.05 mmol scale (105 mg resin), and which yielded 310 mg (89%) of crude peptide resin, 140 mg (85%) of crude peptide, and 2.8 mg of purified peptide, was as follows Asx (3)3.3, Thr (1)0.6, Ser (6)5.9, Ala (2)2.2, Val (5)4.6, Leu (1)1.0, Tyr (2)1.7, Phe (2)2.0, His (1)0.9, Arg (5)5.5.

Analog 3, which was also synthesized on a 0.05 mmol scale (105 mg resin), yielded 320 mg (92%) of crude peptide resin, 145 mg (85%) of crude peptide and 3.5 mg (2.4%) of purified peptide. Purified peptide was homogeneous on TLC. A:$R_f$=0.264, B:$R_f$=0.213. Amino acid analysis Asx (3)3.4, Thr (1)0.7, Ser (6)6.2, Ala (2)2.3, Val (5)4.8, Leu (1)1.1, Tyr (2)1.6, Phe (2)1.9, His (1) 0.7, Arg (5)5.3.

The synthesis of analog 4, which was performed on a 0.25 mmol scale, provided 1 55 g (91%) of crude peptide resin and 690 mg (84%) of crude peptide. Following preparative purification of a 200 mg sample, 8 mg (4%) of homogeneous peptide was isolated which was homogeneous on TLC. A:$R_f$=0.257, B:$R_f$=0.197. Amino acid analysis: Asx (4)3.9, Thr (2)2.0, Ser (3)2.33, Glx (1)1.3, Ala (2)2.0, Val (5)5.3, Leu (1)1.3, Tyr (2)1.7, Phe (2)2.0, His (1)0.4, Lys (3)3.4, Arg (2)2.1.

(e) SYNTHESIS OF VIP ANALOG 20

The synthesis of both an acetylated and a non-acetylated form of analog 20: H-S-D-A-L-F-S-D-A-Y-S-K-L-K-K-S-L-A-L-K-K-Y-L-S-S-L-L-A-(NH$_2$) was initiated by using 4.5 g of a BOC-Ala-BHA resin (p-benzhydrylamine-derivatized polystyrine-1% divinylbenzene, 150–200 mesh) from Colorado Biotechnology Associates (Boulder, Colo., U.S.A.). The quantity of amino acids, prepared as symmetric anhydrides, which were employed is summarized in the following Table I(e):

TABLE I(e)

| CYCLE # | GRAMS OF PROTECTED AMINO ACID | CYCLE # | GRAMS OF PROTECTED AMINO ACID |
|---|---|---|---|
| 1 | 2.32 L | 2 | 2.32 L |
| 3 | 2.75 S | 4 | 2.75 S |
| 5 | 2.32 L | 6 | 4.09 Y |
| 7 | 3.85 K | 8 | 3.85 K |
| 9 | 2.32 L | 10 | 1.76 A |
| 11 | 2.32 L | 12 | 2.75 S |
| 13 | 3.85 K | 14 | 3.85 K |
| 15 | 2.32 L | 16 | 3.85 K |
| 17 | 2.75 S | 18 | 4.09 Y |
| 19 | 1.76 A | 20 | 2.00 D |
| 21 | 1.83 S | 22 | 1.65 F |
| 23 | 1.54 L | 24 | 1.17 A |
| 25 | 2.00 D | 26 | 1.83 S |
| 27 | 3.04 H | | |

Although the synthesis was initiated on a 1.5 mmol scale, it was split after the 19the cycle. The non-acetylated form of analog 20 was then continued on a 1 mmol scale. After the last histidine residue was coupled to the growing analog, one third of the analog preparation was removed. This one third of the preparation was acetylated by treatment with 220 mg of acetyl imidazole in order to form the N-acetylated form of analog 20.

Upon completion of the synthesis of the two forms of analog 20, the following quantities of protected peptide-resin were obtained:
4.52 g for analog 20 (non-acetylated form); and
2.32 g for analog 20 (acetylated form)

Following HF cleavage and extraction, the non-acetylated form of analog 20 was isolated in 48% yield and the acetylated form of analog 20 was isolated in 61% yield.

100 mg of crude non-acetylated analog 20 was purified by preparative HPLC on the Zorbax C-8 column at a flow rate of 15 ml/minute for thirty minutes using 0.1% TFA as a running buffer and a 22–38% acetonitrile gradient. This afforded two highly pure fractions containing non-acetylated analog 20 in 9% overall yield (18.5 mg). Amino acid analysis: Asp (2)2.1, Ser(6)6.3, Ala (4)3.9, Leu (7)6.9, Tyr (2)2.0, Phe (1)1.0, His (1)1.0, Lys (5)4.8.

The acetylated form of analog 20 was cleaved, extracted and purified as described for the non-acetylated form of the analog. The purification of 100 mg of crude acetylated analog 20 resulted in 17.5 mg (11% overall yield) of acetylated peptide which was greater than 98% pure. Amino acid analysis Asp (2)2.0, Ser (6)6.1, Ala (4)3.8, Leu (7)7.2, Tyr (2)2.0, Phe (1)1.0, His (1)1.0, Lys (5)4.9.

(f) SYNTHESIS OF THE CARBOXY-TERMINAL-AMIDATED VIP ANALOG 33

Starting with 2.22 g of p-methylbenzhydrylamine-derivatized polystyrene-1% divinylbenzene resin, the synthesis of analog 33:
H-S-D-A-V-F-S-D-S-Y-S-K-F-R-K-S-J-A-V-K-K-Y-L-S-S-V-L-T-(NH$_2$), amidated at the carboxy-terminus, was performed on a 1.5 mmol scale essentially as described above for the synthesis of analog 20. Recouplings were required after Thr-28, Ser-16, Arg-14, phe-13, Lys-12 and Asp-3. Acetylation of unreacted sites was performed after NorLeu-17 and Arg-14. Arginine was coupled using a 6-fold excess of amino acid and a 6-fold excess of DCC, not as its symmetric anhydride.

HF cleavage of 1 mmol (6.91 g) of the protected peptide-resin and extraction resulted in isolation of the crude analog 33 in 82% yield.

Preparative HPLC of 90 mg of crude product performed with the Zorbax column using 0.1% TFA and a 30–40% CH$_3$CN gradient for 40 minutes resulted in the isolation of 4.5 mg (5% overall yield) of peptide at a purity of greater than 99%. Amino acid analysis results: Asp (2)1.95, Thr (1)1.16, Ser (7)6.59, Ala (2)2.13, Val (3)2.84, Leu (2)2.17, Norleu (1)1.09, Tyr (2)2.05, Phe (2)1.94, His (1)0.98, Lys (4)3.91, Arg (1)1.06.

(g) SYNTHESIS OF THE CARBOXYL-TERMINAL-AMIDATED VIP ANALOGS 28 AND 34–36

Analogs 28 and 34–36, all carboxy-terminal-amidated, are synthesized and purified in substantially the same manner as described above for analog 33, beginning with 2.22 g of p-methylbenzhydrylamine-derivatized polystyrene-1% divinylbenzene resin and employing the appropriate protected amino acid in each cycle of the automated synthesis. After HF cleavage and extraction, the crude analogs are purified by preparative HPLC essentially as in the foregoing Example I(f).

EXAMPLE II

Radioreceptor Assays of Affinities of Analogs for VIP Receptors

Radioreceptor assays were carried out to determine the affinities of analogs of Example I for VIP receptors in rat lung membrane, following Leroux et al., Endocrinology 114, 1506–1512 (1984).

The following buffers were prepared:
Buffer A: 250 mM sucrose, 5 mM MgCl$_2$, 25 mM Tris, pH 7.4
Buffer B: 5 mM MgCl$_2$, 25 mM Tris, pH 7.4
Buffer C: 25 mM Tris, 5 mM MgCl$_2$, 1 mg/ml bacitracin, 2 mg/ml bovine serum albumin ("BSA"), pH 7.4
Phenylmethylsulfonyl fluoride ("PMSF") was added, to a final concentration of 1 mM, to the buffers immediately prior to their use.

Naturally occurring human VIP, human VIP not amidated at the carboxy-terminus, chicken VIP, and guinea pig VIP were synthesized as described in Example I. (Human VIP so synthesized was indistinguishable from that purchased from Peninsula Labs, Inc. (Belmont, Calif., U.S.A.)). Stock solutions of $2.5 \times 10^{-5}$M of the VIP's in $10^{-2}$M acetic acid, 1 mg/ml BSA, and 50 mg/l ascorbic acid were prepared and, for assays, diluted, to appropriate concentrations described below, with Buffer C.

$^{125}$I-labeled, human VIP ($^{125}$I-VIP) was purchased from New England Nuclear (Boston, Mass., U.S.A.). The peptide as purchased was diluted to $10^{-5}$ Ci/ml with Buffer C and stored in 25 μl or 50 μl aliquots at −20° C., which were subsequently diluted with Buffer C, as described below, for the assays.

Rat lung membrane was prepared for the assay as follows, following Leroux et al., supra: Five female Sprague-Dawley rats (200–250 g) were sacrificed and their hearts perfused with iced, phosphate-buffered saline (PBS) through the right atrium (approximately 30 ml PBS per rat). The lungs, which were whitened, were then removed and placed directly in iced PBS and any blood was rinsed from the tissue. The lung tissue was then transferred to a weighing device on ice; blood vessels, fat and the like were removed from the tissue; and the tissue was blotted and weighed. The lung tissue was then transferred to a 50 cm$^3$ Falcon tube with 2 ml of Buffer A per g lung tissue (approximately 25 ml Buffer A) and homogenized at 4° C. 1 minute in a polytron (Brinkmann Instruments Co., Westbury, N.Y., U.S.A.) and then with a glass/teflon homogenizer (approximately 5–6 strokes). The homogenate was filtered through two layers of cheesecloth, and the filtrate was then transferred to tubes for centrifugation at 30,000×g for 10 minutes. The pellets were then resuspended in approximately 70 ml of Buffer B using a glass/teflon homogenizer and the resulting suspensions were again centrifuged at 30,000×g for ten minutes. The resulting pellets were resuspended in 50 ml of Buffer B using a glass/teflon homogenizer. The suspension was divided into 1.0 ml aliquots in microfuge tubes, which were quickly frozen and stored on dry ice until use.

When used, an aliquot of suspension was thawed and microfuged at 4° C. for several minutes to pellet suspended material. The supernatant was carefully removed and the pellet resuspended in 1 ml of Buffer C. Protein concentrations (determined by the Lowry method) of the final suspension were 3.0–3.2 mg/ml.

Prior to use of a VIP receptor-containing suspension in an assay, the protein concentration was adjusted to 2 mg/ml by addition of Buffer C. Then 100 μl of this suspension (2 mg/ml) was combined with 100 μl of solution of $^{125}$I-VIP, 100 μl of solution of the VIP or analog thereof being assayed and 200 μl of Buffer C; consequently, the concentration of protein from the rat lung VIP receptor preparations used in the assays was 0.4 mg/ml.

In the radioreceptor assays, the ability of analog to displace $^{125}$I-VIP from binding in the receptor preparation was measured by a standard procedure. For each analog, and naturally occurring human VIP as standard, a series of solutions, of 500 μl total volume in Buffer C, containing various concentrations of analog or standard (between about $10^{-11}$M and $10^{-6}$M), $^{125}$I-VIP at 100 cpm/μl (about $2 \times 10^{-10}$M), and receptor preparation (0.4 mg protein/ml) were assayed. Each solution was prepared by first combining a solution (100 μl) of analog or standard in Buffer C and a solution in Buffer C of $^{125}$I-VIP (100 μl) with 200 μl Buffer C, then adding receptor suspension (100 μl) (2 mg protein/ml in Buffer C) and incubating for 20 minutes at 37° C. After the incubation, the solutions were chilled on ice and then combined with 2 ml of ice-cold Buffer C. The resulting solutions were then centrifuged at 4° C. at 2500×g for 30 minutes. The supernatant was discarded and the pellet counted by a standard technique. All solutions were run in duplicate.

Non-specific binding of $^{125}$I-VIP was determined from a run with $5\times10^{-7}$M human VIP, far in excess of the approximately $5\times10^{-10}$M required to occupy half of the receptor sites in a rat lung membrane receptor preparation at 0.4 mg protein/ml. Total counts (bound plus unbound) was determined by carrying out an assay without membrane preparation and counting the final solution. Total binding of $^{125}$I-VIP was measured by carrying out the assay with $^{125}$I-VIP but without analog or standard The linear range of the assay was $10^{-10}$M to $10^{-8}$M.

The assays yielded a value, termed "Potency" in the following Table II(a), for each analog, which is the concentration of standard (i.e., human VIP) required to displace $^{125}$I-VIP from half of the receptor sites in the same assay mixture divided by the concentration of the analog required to displace $^{125}$I-VIP from half of the receptor sites in the same assay mixture. In the assays described herein, human VIP at a concentration of about $5\times10^{-10}$M was required to displace half of the $^{125}$I-VIP. All of the novel VIP analogs were effectively able to displace bound $^{125}$I-VIP from rat lung membrane receptors in a dose-dependent manner.

Potencies in receptor binding of some of these VIP analogs, which were calculated from these binding data, are as in Table II(a):

TABLE II(a)

| Peptide | Receptor ED$_{50}$ | Binding Potency |
|---|---|---|
| VIP | 0.5 nm | 1.00 |
| Analog 1 | 290 nm | 0.002 |
| Analog 2 | 250 nm | 0.002 |
| Analog 3 | 700 nm | 0.001 |
| Analog 4 | 450 nm | 0.001 |
| Analog 5 | 1.3 nm | 0.38 |
| Analog 20 (Non-acetylated) | 5.4 nm | 0.10 |
| Analog 20 (Acetylated) | 7.0 nm | 0.07 |
| Analog 33 | 2.0 nm | 0.03 |

Analog 5, which displayed the highest affinity for binding to rat lung VIP receptors, and which had a $K_D$ value of approximately 1 nm, was found to be equal to VIP in its ability to recognize the higher affinity, Class I receptor sites described further below. The above-described results suggest that analog 5 is a good agonist and recognizes functional VIP receptors. The lower overall potency which was calculated for the analogs was determined to be due to a lower binding affinity of such analogs for the more abundant, lower affinity, Class II receptor sites, also described below.

The binding data for VIP were analyzed by Scatchard analysis (Scatchard, G., Ann. N.Y. Acad. Sci. 1:660 (1949)) and by the competitive inhibition analysis described by Bonnevie-Nielsen and Tager, J. Biol Chem. 58:11313 (1983).

Scatchard analysis of the data for VIP-binding, assuming that $^{125}$I-VIP and VIP have identical binding constants, revealed the presence of two classes of binding sites which are defined by the following parameters:

Class I:
$K_{D1}=51\pm5$ pM;
$0.26\pm0.05$ pmol/mg binding capacity; and

Class II:
$K_{D2}=3.2\pm1.1$ nM;
$1.5\pm0.2$ pmol/mg binding capacity.

Dissociation constants for VIP binding to the lung membrane receptors were also calculated by competitive inhibition analysis using the equations of Bonnevie-Nielsen and Tager, supra, assuming $^{125}$I-VIP and VIP interact in the same way with the receptors. Analysis according to Bonnevie-Nielsen and Tager, supra, yielded slightly lower dissociation constants than those obtained by Scatchard analysis:

Class I: $K_{D1}=21\pm13$ pM; and

Class 2: $K_{D2}=1.8\pm0.6$ nM.

The ratio of the Class I receptor binding constant to the Class II receptor binding constant was approximately the same using either method. Dissociation constants, fractions ($F_1$, $F_2$) of label bound to each class of receptors and the fraction ($P_1$, $P_2$) of all receptors represented by each class of receptor were calculated for human VIP and analogs 1, 4 and 5 by the method of Bonnevie-Nielsen and Tager, supra, and are given in Table II(b):

TABLE II(b)

| Parameter | Human VIP (n = 4) | Analog 1 (n = 2) | Analog 4 (n = 2) | Analog 5 (n = 2) |
|---|---|---|---|---|
| $K_{D1}$, nM | 0.021 ± 0.013 | 8.4 ± 0.9 | 3.5 ± 0.5 | 0.011 ± 0.008 |
| $P_1$ | 0.25 ± 0.06 | 0.26 ± 0.08 | 0.30 ± 0.11 | 0.22 ± 0.06 |
| $F_1$ | 0.004 ± 0.002 | 0.006 ± 0.003 | 0.0011 ± 0.0002 | 0.0006 ± 0.0005 |
| $K_{D2}$, nM | 1.8 ± 0.6 | 500 ± 50 | 1600 ± 200 | 6.4 ± 0.2 |
| $P_2$ | 0.75 ± 0.06 | 0.74 ± 0.08 | 0.70 ± 0.11 | 0.78 ± 0.06 |
| $F_2$ | 0.996 ± 0.002 | 0.994 ± 0.003 | 0.9989 ± 0.0002 | 0.9994 ± 0.0005 |

(All values presented are ± one standard deviation.)

All analogs interacted with both classes of receptor sites. The data obtained from these calculations indicates that analog 5 has an affinity comparable to, or greater than, VIP for the high affinity class of rat lung membrane receptors. The fact that $P_1$ and $P_2$ are essentially the same for both VIP and analog 5 indicates that the binding of $^{125}$I-VIP to receptors is not altered by the competing ligand. Thus, it appears that the lower overall potency of analog 5 was due to a lower binding affinity for the more abundant, lower affinity, Class II receptor sites. This analysis indicates that analog 5 has the unexpected property of being a more selective agonist of VIP action than the native hormone.

Results of receptor binding assays support the hypothesis that a pi-helical domain from amino acid residues 6 through 28 provides the structural requirements for the binding of VIP to its membrane receptors.

EXAMPLE III

Bioactivity Assay of VIP Analogs

The bioactivities of analogs of Example I, chicken vasoactive intestinal peptide ("chicken VIP"), and the analog of human VIP without amidation at the carboxyterminus were determined, relative to that of naturally occurring human VIP, by an amylase-release assay employing dispersed guinea pig pancreatic acinar cells. The bioassay, which was essentially that described by Peikin et al., Am. J. Physiol 235, E743-E749 (1978), measures the secretion of amylase from dispersed guinea pig pancreatic acini.

For the assays conducted each day, dispersed acinar cells, free of debris, were freshly prepared from a pancreas of a male or female guinea pig (120-150 gm), following generally the method described by Peikin et al., supra.

The procedure employed a "standard incubation medium," which consisted of 95 mM NaCl; 6 mM KCl; 2.0 mM $NaH_2PO_4$; 5 mM each of sodium pyruvate, sodium fumarate and sodium glutamate; 0.5 mM $CaCl_2$, 1.0 mM $MgCl_2$, 11.5 mM glucose, 0.05 mg/ml glutamine; amino acids and vitamins from Eagle's Minimum Essential Medium at their concentration in such Eagle's Medium; 25 mM HEPES; 0.08 mg/ml soybean trypsin inhibitor (Sigma); pH 7.4.

The animal was sacrificed, its pancreas removed and the pancreas trimmed of fat, blood vessels, duodenum and the like. With a syringe with a 25 gauge needle, 10.0 ml of collagenase solution (standard incubation medium with 0.05 mg/ml C. histolyticum collagenase (Cooper Biomedical, CLSPA) and 2 mg/ml BSA (cyrstalline) (from Miles Diagnostics) was injected into the pancreas, which was then transferred to a 25 ml flask, gassed with 100% $O_2$, and shaken on a shaker as rapidly as possible for 10 minutes at 37° C. Then the liquid was poured off and replaced with another 5.0 ml of collagenase solution, and the gassing with 100% $O_2$ and shaking for 10 minutes at 37° C. were repeated. The replacement of liquid, gassing with 100% $O_2$ and shaking at 37° C. were again repeated. If, by visual inspection, digestion appeared to be incomplete, vigorous shaking by hand with 1 minute incubation at 37° C. were repeated until digestion was complete. The mass was then broken up further by passing chunks through a large bore serological pipette, and then a small bore pipette. Very large chunks, fur and debris were removed with a long Pasteur pipette. Then half of the resulting acinar cell suspension was placed into each of two 15 ml clear, polystyrene tubes, each containing 4.0 ml of 4.0% BSA solution (standard incubation medium with 40 mg/ml BSA (crystalline) and 2 mM, rather than 0.5 mM, $CaCl_2$). Both combinations were mixed thoroughly and debris was again removed. The resulting suspensions were spun at medium speed in a tabletop centrifuge for 30 seconds, the supernatants were discarded, and the pellets were resuspended in 4.0 ml of 4.0% BSA and 4.0 ml of 0.2% BSA solution (standard suspension medium with 2 mg/ml BSA (crystalline) and 2 mM, rather than 0.5 mM, $CaCl_2$), the suspension was again cleaned of debris, and then spun as above with the tabletop centrifuge. The supernatants were discarded and the pellets again washed with 4.0 ml of 4% BSA solution and repelleted as above with the tabletop centrifuge Again, the supernatants were discarded and the pellets were carried into one 250 ml Erlenmeyer flask, to which 50.0 ml of 1% BSA solution (standard incubation medium with 10 mg/ml BSA (crystalline) and 5 mM theophylline)) had been added. When the cells were not used immediately, the suspension was gassed with 100% $O_2$. The preparation was acceptable for use in an assay only if the cells were fine and well dispersed and there was nothing visible in the preparation other than cells.

VIP analog to be assayed was dissolved in 1% BSA solutions at concentrations of $10^{-5}M$, $10^{-6}M$, $10^{-7}M$, $10^{-8}M$, and $10^{-9}M$. Suitable volumes of these solutions were then combined with 500 $\mu l$ of the acinar cell suspension so that duplicate samples of each of the following concentrations of analog in the suspensions resulted: 0 (control, 500 $\mu l$ acinar cell suspension, no VIP); $10^{-11}M$; $10^{-10}M$; $3 \times 10^{-10}M$; $10^{-9}M$; $3 \times 10^{-9}M$; $10^{-8}M$; and $10^{-7}M$. The resulting suspensions were incubated for 30 minutes at 37° C.; no gassing or capping was employed.

The "0" time point amylase release values were obtained by spinning, at high speed in a refrigerated tabletop centrifuge for 30 seconds, two samples, each of 400 $\mu l$ of unincubated acinar cell suspension, and then transferring 50 $\mu l$ from each sample to another tube for analysis. These are termed "0 value tubes."

The "total amylase" was determined by combining each of two 500 $\mu l$ samples of acinar cell suspension in a tube with 5 ml of lysing solution (prepared by combining 1.0 ml of 100 mM $CaCl_2$, 1.45 g $NaH_2PO_4$, 0.1 g sodium dodecylsulfate, 0.1 g BSA (crystalline) in 100 ml $H_2O$ and adjusting pH to 7.8 with NaOH). The tube was covered with parafilm and vortexed vigorously. Then 150 $\mu l$ of the solution was transferred to each of two other tubes.

From each of the incubated samples, 400 $\mu l$ was removed to a microfuge tube and spun for 30 seconds at high speed on a tabletop centrifuge. Then, two 50 $\mu l$ aliquots were transferred to different tubes (50 $\mu l$ each); these are termed "experiment tubes."

Then 100 $\mu l$ of lysing solution was added to each of the "0-value" tubes and each of the "experiment" tubes.

3 Phadebas Amylase Assay Tablets (Pharmacia, Inc., Piscataway, N.J., U.S.A.) were dissolved in 25 ml of amylase reagent buffer (20 mg $NaN_3$, 1.14 gm NaCl and 1.12 gm $NaH_2PO_4$ in 500 ml $H_2O$, pH is adjusted to 7.0 with NaOH). While the Phadebas solution was still stirring, 1.0 ml was taken and added to each of the "0-value" tubes and "experiment" tubes. The tubes were then incubated at 37° C. until color development occurred (approximately 15 minutes). (It was made certain that starch substrate for the assay did not become limiting.) When color had developed sufficiently that there was a clear difference between the "no VIP" experiment tubes and the experiment tubes with VIP, the reactions were stopped by adding to each tube 2.75 ml of 0.045M NaOH. Each sample was then centrifuged at 2200×g for 5 minutes and the optical density of each sample was measured at 620 nm. The fraction of amylase released was then calculated as:

$$\frac{(O.D.)_{unknown} - (O.D.)_{\text{"0" tube}}}{[3.67 \times (O.D.)_{Total\ Amylase}] - (O.D.)_{\text{"0" tube}}}$$

where "O.D."$_{\text{"0" tube}}$ is the average O.D. of the "0" value tubes; "O.D."$_{total\ amylase}$ is the average O.D. of the "total amylase" tubes; and 3.67 is a dilution factor for the "total amylase" tubes. The average was determined of the fractions of amylase released from the "experiment tubes" for each concentration of analog, and this average was taken as the fraction released due to the analog at the involved concentration.

In plots of fraction of amylase released against logarithm of VIP analog concentration, it has been found that, for all analogs, the fraction released plateaus at about the same fraction. The "ED$_{50}$" for an analog was taken to be the concentration that caused a release of a half of the maximum released, (i.e., the plateau value). The "potency" of an analog, compared with naturally occurring human VIP (i.e., ED$_{50}$ for the human VIP standard divided by ED$_{50}$ for the analog) is a measure of the bioactivity of the analog relative to that of the standard. The results obtained are listed in Table III:

TABLE III

| Analog | Amylase Release Assay | |
|---|---|---|
| | ED$_{50}$ | Potency |
| Human VIP | 30 pM | 1.0 |
| Human VIP, non-amidated | 70 pM | 0.4 |
| Chicken VIP | 60 pM | 0.5 |
| 1 | 14 nM | 0.002 |
| 2 | 5 nM | 0.005 |
| 3 | 30 nM | 0.001 |
| 4 | 6 nM | 0.005 |
| 5 | 90 pM | 0.33 |
| 7 | 30 nM | 0.001 |
| 9 | 42 nM | 0.0007 |
| 20, non-acetylated | 3.5 nM | 0.01 |
| 20, acetylated | 13 nM | 0.0025 |

All of the analogs assayed were able to elicit maximal stimulation of alpha-amylase secretion in dispersed guinea pig pancreatic acinar cells comparable to human VIP. In all cases, potencies in receptor binding and generation of cellular response were parallel, indicating that all of the analogs were interacting with functional VIP receptors.

In the guinea pig pancreatic acini, the stimulation of amylase secretion appeared to be linked to the high affinity class of VIP receptors, as assessed by the high sensitivity of VIP and analog 5 in effecting this process. The fact that, in this assay, VIP was more potent than analog 5 may reflect differences among receptors of various tissue types and species.

EXAMPLE IV

Analog Stability Against Proteolytic Degradation

The stability of naturally occurring, human VIP and various analogs described in Example I was assessed by determining their ability to resist degradation effected by enzymes when incubated with a crude rat lung homogenate.

For the assay, the lungs were taken from a male Sprague-Dawley rat and were perfused with ice-cold phosphate-buffered saline, as described in Example II. The whitened lungs were polytroned and then homogenized in Degradation Assay Buffer (25 mM Tris, 5 mM MgCl$_2$, pH 7.4), and the homogenate was filtered through cheesecloth. The filtrate was then diluted to a final volume of 500 ml with Degradation Assay Buffer, to yield the crude lung homogenate.

Resistance to degradation was measured by determining the half-life of the human VIP or analog in the crude lung homogenate. To determine these half-lives, 0.05 ml of a 10$^{-4}$M peptide solution was added to 0.45 ml of the homogenate, and the mixture was incubated at 37° C. After incubation for the desired time period, sodium dodecyl sulfate (SDS) was added to the sample to a final volume of 2% (v/v) and the sample was placed in a 100 C constant boiling water bath and boiled for 5 minutes, and then acidified with glacial acetic acid (10% final volume) and, finally, cooled rapidly by being placed on dry ice. The addition of SDS prior to the boiling step and the performance of the boiling step in a constant boiling water bath indicates a greater stability of the peptides. Apparently, a significant amount of peptide degradation occurrs during the time which is required to heat and denature the proteolytic enzymes in the samples (inactivation step). The sample was then microfuged at 4 C for 15 minutes, and the supernatant analyzed for peptide content by HPLC. Test reactions indicated that no decomposition products from the homogenate coeluted with the intact human VIP or any intact analog. The assay results were analyzed by linear regression to provide the results in Table IV below, which are expressed as half-life of the intact human VIP or analog, and which indicate that the stabilities of the analogs were comparable to that of human VIP under the conditions employed.

TABLE IV

| ANALOG | HALF-LIFE (minutes) |
|---|---|
| Human VIP | 30 ± 10 |
| 1 | 26 ± 6 |
| 2 | 19 ± 8 |
| 3 | 18 ± 5 |
| 4 | 34 ± 11 |
| 5 | 31 ± 20 |

EXAMPLE V

Relaxation of Guinea Pig Trachea and Rat Stomach Fundus Strips

VIP analogs 5, 20 (acetylated) and 20 (nonacetylated) were each tested, and compared to human VIP in terms of potency, for their ability to cause relaxation of guinea pig trachea and rat stomach fundus strips, two tissues known to be sensitive to VIP.

Guinea pig trachea and rat stomach tissue were each separately cut into 2 cm × 2 mm strips, suspended in a 5 ml organ bath containing Krebs solution, maintained at 37° C. and equilibrated with 95% O$_2$ and 5% CO$_2$ (Piper et al., Nature 225:1144 (1970); Said, S.I., Am. J. Med. 57:453 (1974); and Hamasaki et al., Trans. Assoc. Am. Physicians 96:406 (1983)).

Peptides were tested by adding them to the organ bath. After the full response was obtained and a new muscle tone was reached, the bath was rinsed with Krebs solution to wash the peptide off. The duration of action was measured from the start of the wash until the tissue returned to 50% of the distance towards the baseline tension. The relaxation of the two tissues was measured in gram equivalent, using isometric pressure transducers. The results of these tests are indicated in the following Tables V(a) and V(b).

TABLE V(a)
RELAXATION OF GUINEA PIG TRACHEA

| Peptide | Final Concentration (μg/ml) | Relaxation (g Equivalent) | Duration (50% Return to Baseline) (Min.) | Potency |
|---|---|---|---|---|
| Analog 20 (Non-Ac) | 10 | >0.7 | 10 | |
| | | | | 0.1 |
| | 2 | 0.3 | 8 | |
| Analog 20 (Ac) | 10 | >0.6 | 14 | |
| | | | | 0.2 |
| | 1 | 0.3 | 6 | |
| Analog 5 | 10 | >0.8 | 19 | |
| | | | | 0.33 |
| | 1 | 0.55 | 11 | |
| Human VIP | 1 | >0.8 | 12 | |
| | | | | 1.0 |
| | 0.2 | 0.3 | 7 | |

> - Indicates that relaxation was greater than the number given and was off of the scale on the recorder.
Non-Ac - Indicates non-acetylated.
Ac - Indicates acetylated.

TABLE V(b)
RELAXATION OF RAT STOMACH

| Peptide | Final Concentration (μg/ml) | Relaxation (g Equivalent) | Duration (50% Return to Baseline) (Min.) | Potency |
|---|---|---|---|---|
| Analog 20 (Non-Ac) | 1 | 0.7 | 11 | |
| | | | | 0.5 |
| | 0.2 | 0.4 | 6 | |
| Analog 20 (Ac) | 1 | 0.8 | 17 | |
| | | | | 0.5 |
| | 0.2 | 0.5 | 4 | |
| Analog 5 | 1 | >0.7 | 30 | |
| | 0.1 | >0.9 | 13 | 1.0 |
| | 0.05 | 0.4 | 6 | |
| Human VIP | 0.1 | 0.6 | 22 | 1.0 |

> - Indicates that relaxation was greater than the number given and was off of the scale on the recorder.
Non-Ac - Indicates non-acetylated.
Ac - Indicates acetylated.

Analogs 5, 20 (non-acetylated), and 20 (acetylated) all exhibited a VIP-like, dose-dependent, sustained relaxation of guinea pig trachea and rat stomach fundus strips. Analog 5 was equipotent to human VIP in the rat stomach strip assay. The durations of action of the analogs were similar to that of human VIP.

The potencies of both the acetylated and the non-acetylated form of analog 20 in terms of binding to rat lung receptors and relaxation of guinea pig trachea were comparable. However, in the guinea pig pancreas, the peptides were 100 to 400 times lower in potency than human VIP, whereas in the rat stomach, the potencies were one-half that of human VIP. The results of these two bioassays suggest that analog 20 has the surprising ability to differentiate between VIP receptors in a tissue-specific manner.

EXAMPLE VI

An analysis of the data presented above on receptor binding in lung membrane preparations, for human VIP and analogs 5, 20 and 33, in conjunction with the hypothesis (supported by the foregoing data on all of the analogs tested) that the secondary structure of residues 6-28 of VIP, when interacting with its receptor, is an amphiphilic pi-helix, suggests that receptor binding affinity (and bioactivity) would be increased with the amino acid(s) at each of the positions, in a 28 amino acid VIP analog, indicated in the following Table VI:

TABLE VI

| Position in Sequence* | Amino Acid to Increase Receptor-Binding Affinity |
|---|---|
| 7 | T |
| 9 | N, T or A |
| 12 | R |
| 13 | L |
| 14 | K or J |
| 19 | V |
| 26 | V |
| 28 | T |

*The amino-terminal amino acid is at position 1.

While the invention has been illustrated herein with some specificity, it will be apparent to those skilled in the art that various modifications and variations can be made in the specifics without departing from the spirit of the invention. Such modifications and variations are also within the scope of the invention as described and claimed herein.

What is claimed is:

1. A VIP analog with a formula selected from the group consisting of:

H-S-D-A-V-F-T-D-A-Y-S-R-L-J-R-S-J-A-V-R-R-Y-L-S-S-V-L-T-(NH$_2$); and

H-S-D-A-V-F-T-S-T-Y-S-R-L-J-R-S-J-A-V-R-R-Y-L-S-S-V-L-T-(NH$_2$);

wherein i is 0 or 1, wherein 0 indicates that the peptide is not carboxy-terminal-amidated and 1 indicates that the peptide is carboxy-terminal-amidated, or a pharmaceutically acceptable salt thereof.

2. An analog according to claim 1 with the formula: H-S-D-A-V-F-T-D-A-Y-S-R-L-J-R-S-J-A-V-R-R-Y-L-S-S-V-L-T-(NH$_2$)$_i$, or a pharmaceutically acceptable salt thereof.

3. An analog according to claim 1 with the formula: H S-D-A-V-F-T-S-T-Y-S-R-L-J-R-S-J-A-V-R-R-Y-L-S-S-V-L-T-(NH$_2$)$_i$, or a pharmaceutically acceptable salt thereof.

4. An analog according to claim 2 wherein i is 1, or a pharmaceutically acceptable salt thereof.

5. An analog according to claim 3 wherein i is 1, or a pharmaceutically acceptable salt thereof.

* * * * *

UNITED STATES PATENT AND TRADEMARK OFFICE
CERTIFICATE OF CORRECTION

PATENT NO. : 4,939,224   Sheet 1 of 2
DATED : July 3, 1990
INVENTOR(S) : Gary F. Musso, et al.

It is certified that error appears in the above-identified patent and that said Letters Patent is hereby corrected as shown below:

| | |
|---|---|
| Column 4, Line 46: | In the sequence of Analog 2 between the 7-position, "S", and the 8-position, "D", delete the " " (space) and insert -- - -- (a hyphen). |
| Column 4, Line 58: | In the sequence of Analog 5, change the 12-position "T" to --R--. |
| Column 5, Line 2: | In the sequence of Analog 8, change the 9-position "H" to --N--. |
| Column 5, Line 11: | In the sequence of Analog 10, change the 15-position "I" to --K--. |
| Column 14, line 26: | Change "1 61" to --1.61--. |
| Column 14, line 41: | Before "minutes", insert --50--. |
| Column 14, lines 55-56: | Change "1 31" to --1.31--. |
| Column 15, line 63: | Change "1 55" to --1.55--. |
| Column 16, line 35: | Change "19the" to --19th--. |
| Column 19, line 67: | Change "1:660" to --51:660--. |
| Column 20, line 2: | Change "58:11313: to --258:11313--. |
| Column 22, line 64: | Change "O.D." to --O.D.-- (second occurence). |

UNITED STATES PATENT AND TRADEMARK OFFICE
CERTIFICATE OF CORRECTION

PATENT NO. : 4,939,224  Sheet 2 of 2
DATED : July 3, 1990
INVENTOR(S) : Gary F. Musso, et al.

It is certified that error appears in the above-identified patent and that said Letters Patent is hereby corrected as shown below:

| | |
|---|---|
| Column 24, line 9: | After "100", insert --°-- (degree sign). |
| Column 24, line 20: | After "4" insert --°-- (degree sign). |
| Column 28, line 2: | In the analog sequence, insert -- - -- (a hyphen) between the 1-position "H" and the 2-position "S". |

Signed and Sealed this

Twenty-fourth Day of September, 1991

Attest:

HARRY F. MANBECK, JR.

*Attesting Officer*  *Commissioner of Patents and Trademarks*